United States Patent [19]

Koester et al.

[11] Patent Number: 4,932,994
[45] Date of Patent: * Jun. 12, 1990

[54] EVAPORATION INHIBITORS

[75] Inventors: Josef Koester; Adolf Asbeck; Holger Tesmann, all of Duesseldorf; Margarete Gruenert, Kaarst; Konrad Albrecht, Kelkheim; Paul Bittner, Kriftel; Fritz Keim, Hofheim, all of Fed. Rep. of Germany

[73] Assignee: Henkel Kommanditgesellschaft auf Aktien, Duesseldorf, Fed. Rep. of Germany

[*] Notice: The portion of the term of this patent subsequent to Dec. 27, 2005 has been disclaimed.

[21] Appl. No.: 798,219

[22] Filed: Nov. 14, 1985

[30] Foreign Application Priority Data

Nov. 14, 1984 [DE] Fed. Rep. of Germany ....... 3441587

[51] Int. Cl.$^5$ ........................................... A01N 25/02
[52] U.S. Cl. ................................. 71/79; 71/DIG. 1; 106/271; 47/DIG. 11
[58] Field of Search .............. 71/DIG. 1, 79; 106/271; 47/DIG. 11; 514/772

[56] References Cited

U.S. PATENT DOCUMENTS

| 2,284,970 | 6/1942 | Avery | 47/58 |
|---|---|---|---|
| 2,580,653 | 1/1952 | Bridgeman | 71/2.6 |
| 3,154,402 | 10/1964 | Salvesen et al. | 71/DIG. 1 |
| 3,260,589 | 7/1966 | Salvesen | 71/2.6 |
| 3,791,839 | 2/1974 | Cushman et al. | 106/268 |
| 3,847,641 | 11/1974 | Cushman et al. | 117/3 |
| 3,873,689 | 3/1975 | Frensch et al. | 424/78 |
| 3,890,158 | 6/1975 | Cushman et al. | 106/271 |
| 4,329,390 | 5/1982 | Danner | 106/271 |

FOREIGN PATENT DOCUMENTS

| 1296457 | 5/1969 | Fed. Rep. of Germany. |
|---|---|---|
| 1542682 | 7/1970 | Fed. Rep. of Germany. |
| 1767100 | 8/1971 | Fed. Rep. of Germany. |
| 2205590 | 8/1973 | Fed. Rep. of Germany. |
| 2053631 | 4/1971 | France. |
| 699196 | 3/1951 | United Kingdom. |
| 897644 | 9/1959 | United Kingdom. |
| 926862 | 6/1961 | United Kingdom. |
| 1072045 | 11/1963 | United Kingdom. |
| 1062457 | 8/1964 | United Kingdom. |
| 1136082 | 1/1966 | United Kingdom. |
| 1274921 | 7/1969 | United Kingdom. |
| 1307313 | 4/1970 | United Kingdom. |
| 1367183 | 8/1972 | United Kingdom. |

OTHER PUBLICATIONS

European Patent Search Report.

Primary Examiner—Catherine L. Mills
Attorney, Agent, or Firm—Ernest G. Szoke; Wayne C. Jaeschke; Real J. Grandmaison

[57] ABSTRACT

An evaporation inhibitor, having particular use with spray mixtures of agricultural chemicals applied by the low-volume method, in the form of a paraffin-containing aqueous dispersion or a self-emulsifying solution in an organic solvent, and having the following composition:

| from 15 to 40% | by weight of paraffin waxes or a wax mixture containing paraffin waxes having a dropping point of from 35 to 80° C., |
|---|---|
| from 4 to 20% | by weight of nonionic and/or anionic emulsifiers, |
| from 35 to 81% | by weight of water and/or an organic solvent which is one or more of a hydrocarbon, an ester and a ketone, which have boiling points of from 70 to 280° C., and |
| from 0 to 5.5% | by weight of other auxiliaries. |

21 Claims, No Drawings

EVAPORATION INHIBITORS

BACKGROUND OF THE INVENTION

1. Field of the Invention

The present invention relates to evaporation inhibitors, and to methods for using such inhibitors to reduce the evaporation of water from spray mixtures of agricultural chemicals.

2. Description of Related Art

Agricultural chemicals are widely used nowadays to safeguard the growth and yield of crops, and are usually applied by airplane to cover large areas under cultivation. To minimize the costs involved, every effort is made to keep the quantities of water required for diluting the commercial concentrates as small as possible and to apply high concentrations of active compounds in small amounts. Today, quantities of 5–50 liters/ha are applied by the low-volume (LV) method using known commercial products, such as wettable powders (WP), suspended concentrates (SC) or solvent-containing emulsifiable concentrates (EC) which are normally sprayed in suspension in 300–600 liters of water/ha using ground appliances.

The smaller the quantities of spray mixture applied per unit area, the finer the droplets applied have to be to obtain satisfactory coverage of the crops. This plus the high concentration of the spray mixtures has hitherto created the main obstacle to application of the low-volume method, particularly under sub-tropical and tropical climatic conditions, namely, the water evaporates too quickly due to the large surface area of the fine droplets, so that the active compound can readily be carried away by the wind. Losses are incurred through drifting and, depending on the plant protection agent used, may even cause damage to adjacent crops. Accordingly, exact dosage is difficult, particularly where the spray mixtures are applied from aircraft. Damage to the environment or losses of crop yield may have to be accepted.

In addition, heavy foaming can occur during preparation of the spray mixture with the greatly reduced quantities of water, because the dispersants and wetting agents in the wettable powders or concentrated dispersions are then present in correspondingly higher concentrations. The product foams out of the spray tanks unless the filling level is greatly reduced.

The above spray mixtures of agricultural chemicals are prepared from commercial concentrates by dispersion or emulsification in the desired quantity of water. The concentrates are either self-emulsifying solutions in an organic solvent (EC) or wettable powders (WP) or suspended concentrates (SC).

The agricultural chemicals used can be one or more of insecticides, fungicides, virucides, herbicides, acaricides, dessicants, growth regulators, ripening accelerators, repellents, pheromones, leaf fertilizers, defoliants, etc. In addition, the concentrates can optionally contain dispersants, emulsifiers, wetting agents, defoamers, stickers, carriers and pigments for obtaining a marking effect.

An object of the present invention is to reduce the evaporation of water in the low-volume method of applying agricultural chemicals in the form of spray mixtures. Measures in that direction are the subject of German Application No. 22 05 590, although the mineral-oil-based evaporation inhibitors claimed therein are not sufficiently effective under sub-tropical and tropical climatic conditions. In addition, it is known from U.S. Pat. No. 3,791,839 that the release of water from living plants, particularly during growth in dry climates, can be reduced by applying to the surface of the plants an aqueous emulsion which, in addition to paraffin wax and emulsifier, contains vaseline-like hydrocarbons (petrolatum) as an essential ingredient. However, the function of these emulsions is not to reduce the evaporation of spray mixtures of plant protection agents during spraying by the low-volume method.

DESCRIPTION OF THE INVENTION

Other than in the operating examples, or where otherwise indicated, all numbers expressing quantities of ingredients or reaction conditions used herein are to be understood as modified in all instances by the term "about."

The present invention relates to an evaporation inhibitor (EI) for spray mixtures of agricultural chemicals applied by the low-volume method in the form of a paraffin containing aqueous dispersion or a self-emulsifying solution in an organic solvent. The evaporation inhibitor of the invention has the following composition:

| | |
|---|---|
| from 15 to 40% | by weight of paraffin waxes or a wax mixture containing paraffin waxes having a dropping point of from 35 to 80° C., |
| from 4 to 20% | by weight of nonionic and/or anionic emulsifiers, |
| from 35 to 81% | by weight of water and/or an organic solvent which is one or more of a hydrocarbon, an ester and a ketone, wherein the organic solvent has a boiling point in the range of from 70 to 280° C., and |
| from 0 to 5.5% | by weight of other auxiliaries. |

The present invention also relates to a process for reducing the evaporation of water from spray mixtures of agricultural chemicals during application by the low-volume method, wherein from 1 to 15% by weight and preferably from 5 to 10% by weight of an evaporation inhibitor of the invention is added to the spray mixtures adjusted to an "in-use" concentration.

The inhibitors of the invention can be present in the form of solutions of the wax and emulsifier constituents in the organic solvent. Solutions such as these are temperature-stable and storable and, when stirred into water or spray mixtures adjusted to the "in-use" concentration, form dispersions which are sufficiently stable under normal practical conditions.

However, the inhibitors of the invention are preferably used in the form of concentrated aqueous dispersions because, in that form, they are easier to incorporate in the spray mixtures due to the absence or substantial absence of solvent. The dispersions are prepared, for example, by melting the constituents to be dispersed (paraffin wax or wax mixture, emulsifiers, optionally organic solvents) together and then adding the desired amount of water and, optionally, other auxiliaries. In the case of relatively high melting wax mixtures, it is best to stir the molten wax mixture into the water heated to 80°–100° C., followed by rapid cooling. The dispersions show high temperature stability and high stability in storage, enabling them to be used even under sub-tropical and tropical climatic conditions.

The preferred inhibitors of the invention are used in the form of aqueous dispersions having the following composition:

| | |
|---|---|
| from 15 to 40% | by weight of a paraffin wax or of a mixture of paraffin waxes having different dropping points in the range of from 35 to 70° C., or of a mixture of such paraffin waxes with one or more microcrystalline waxes having dropping points of from 50 to 90° C., wherein the paraffin waxes make up at least 50% by weight of the wax mixture, |
| from 4 to 20% | by weight and preferably from 4 to 14% by weight of one or more nonionic emulsifiers, |
| from 0 to 10% | by weight and preferably from 1 to 7% by weight of one or more anionic emulsifiers, wherein the nonionic emulsifiers make up at least 50% by weight of the total emulsifiers present, |
| from 35 to 81% | by weight of water, |
| from 0 to 10% | by weight of xylene or cyclohexanone or a petroleum fraction having a boiling point in the range of from 145 to 210° C., or an ester having a boiling point in the range of from 70 to 280° C., |
| from 0 to 5% | by weight of one or more hydrotropes, |
| from 0 to 0.5% | by weight of one or more inorganic salts. |

The aqueous dispersions are particularly suitable for use in spray mixtures based on solvent-containing emulsifiable concentrates (EC) and wettable powders (WP). The spray mixtures are prepared simply by stirring the aqueous dispersion into the spray mixtures adjusted to the in-use concentration. The aqueous dispersion is added to the spray mixture in a quantity of from 1 to 15% by weight and preferably in a quantity of from 5 to 10% by weight.

In the treatment of large areas, the spray mixtures are generally applied by airplane in the form of a very fine spray mist, although portable or mobile appliances can be used for smaller areas.

By virtue of the presence in them of waxes or wax mixtures specifically adapted to the particular "in-use" conditions, the claimed evaporation inhibitors greatly inhibit the evaporation of water from the droplets of spray mist during application. It is essential that the dropping point of the paraffin wax or wax mixture should be from 10° to 40° C. and preferable at least 15° C. above the particular air temperature prevailing during application. In this way, the droplets largely retain their weight, resulting in an increased rate of fall and less drifting under the effect of wind. This leads to a better effect of the plant treatment agents and hence to higher crop yields.

In addition, the quantities of active compound can also be reduced. Moreover, the fact that the quantity of liquid is maintained in the droplets of spray mixture avoids undesirable concentration of the active substances, ensuring slow release which can have a positive effect on the phytotoxicity of the agents used. Furthermore, the waxes present in the inhibitors have a foam-damping effect, thus preventing excessive foaming during preparation of the spray mixtures and their introduction into tanks and the like.

Compositions containing petrolatum such as those disclosed in U.S. Pat. No. 3,791,839 are not useful for the purposes of the present invention, i.e., the necessary reduction of evaporation of water from spray mixtures of agricultural chemicals is not achieved during spraying when petrolatum is a component of the compositions. In addition, compositions as disclosed in U.S. Pat. No. 3,791,839 are not generally suitable for mixing with emulsion spray mixtures of agricultural chemicals due to interference with the stability of the emulsions, especially in hot climates. Furthermore, the presence of petrolatum adversely affects the storage stability of the evaporation inhibitors of the invention, particularly during extended storage in hot climates.

The paraffin waxes used in the evaporation inhibitors of the invention consist essentially of linear $C_{20}$–$C_{40}$ hydrocarbons having an average molecular weight of from 280 to 560. Paraffin waxes such as these have dropping points of from 35° to 80° C. and preferably from 35° to 70° C. To ensure that the evaporation-inhibiting effect is achieved, even at relatively high air temperatures, it is best to combine paraffin waxes having different dropping points or paraffin waxes and microcrystalline waxes. In either case, however, the paraffin waxes must make up at least 50% by weight of the wax mixture.

Microcrystalline waxes consist mainly of naphthenes having long side chains together with isoparaffins and small quantities of other aliphatic and aromatic hydrocarbons. The individual constituents contain from 30 to 60 carbon atoms in the molecule. The waxes have average molecular weights of from 580 to 700 and dropping points of from 50° to 90° C.

The emulsifiers used are preferably nonionic surfactants or surfactant mixtures, including for example the sorbitan esters of higher fatty acids and long-chain alkyl glycosides and also alkylene oxide adducts with higher, $C_{10}$–$C_{24}$, linear monofunctional and polyfunctional alcohols, alkylphenols, long-chain carboxylic acids, carboxylic acid amides and hydroxy fatty acids as well as with fatty acid glycerol or sorbitan esters and long-chain alkyl glycosides. The adducts of from 2 to 50 moles of ethylene oxide with long-chain, more especially $C_{12}$–$C_{18}$ primary alcohols and fatty acids are preferably used. To improve the temperature stability of the aqueous inhibitor dispersions, it is advisable to combine two or more alkylene oxide adducts differing in their degree of alkoxylation with one another. A mixture of ethylene oxide adducts with $C_{12}$–$C_{18}$ fatty alcohols or alkylphenols consisting of

| | |
|---|---|
| from 10 to 40% | by weight of adducts containing from 1 to 4 moles of ethylene oxide, |
| from 25 to 70% | by weight of adducts containing from 4 to 10 moles of ethylene oxide, |
| from 5 to 35% | by weight of adducts containing from 10 to 50 moles of ethylene oxide, | has proved to be particularly effective. The above percentages by weight are based on the total weight of the adduct mixture.

The dispersions can be further stabilized by replacing part of the nonionic emulsifiers by anionic emulsifiers. Suitable anionic emulsifiers are the alkali metal, ammonium, amine and alkaline-earth metal salts of long-chain alkyl sulfates, sulfonates and phosphoric acid partial esters. Particularly suitable anionic emulsifiers are salts of sulfuric acid semiesters or phosphoric acid partial esters of linear alcohols or alkylphenols containing from 12 to 18 carbon atoms or of polyglycol monoalkylethers containing from 12 to 18 carbon atoms in the alkyl group and olefin sulfonates, ester sulfonates and alkyl sulfonates containing from 12 to 20 carbon atoms, alkylbenzene sulfonates containing from 6 to 16 carbon atoms in the alkyl groups, sulfonates of polyglycol monoalkylethers and salts of polyglycol monoalkylether carboxylic acids containing from 12 to 18 carbon atoms in the alkyl groups. Of these surfactants, alkylbenzene sulfonates and alkane sulfonates are preferably used. The emulsifiers are used in a total quantity of from 4 to 20% by weight and more preferably from 4 to 14% by weight, based on the inhibitor dispersion or solution. Where anionic emulsifiers are present, they preferably make up at least 0.5% by weight and more especially at least 1.0% by weight of the inhibitor as a whole. The nonionic emulsifiers should preferably make up at least 50% by weight of the total quantity of emulsifiers.

The organic solvents optionally present in the inhibitor formulations are liquid hydrocarbons, esters or ketones having boiling points of 70° to 280° C., for example light mineral oils, toluene, liquid fatty acid methylesters and the like. Preferred solvents are xylene, cyclohexanone, and petroleum fractions boiling at temperature in the range of from 145° to 210° C.

Other auxiliaries, which can be used as desired in a total quantity of up to 5.5% by weight, based on the inhibitor dispersions, include dyes, viscosity regulators, foam regulators, preservatives, inorganic salts, pH regulators, hydrotropes and other dispersion aids. Of particular importance to the dispersions in this respect are hydrotropes and salts which influence the structure of the aqueous component of the dispersion and thus enable viscosity and degree of dispersion to be regulated. Preferred hydrotropes are non-surface-active salts of aromatic sulfonic acids, such as sodium cumene sulfonate, and of sulfuric acid semiesters with $C_6$-$C_{10}$ alcohols. The hydrotropes need only be used in quantities of up to 5% by weight. Suitable inorganic salts, which may be added in quantities of up to 0.5% by weight, are in particular the sodium or potassium salts of mineral acids.

The type of plant protection agents used in the spray mixtures is not critical to the use of the evaporation inhibitors (EI) according to the invention. For example, spray mixtures which have been prepared from commercial concentrates may contain one or more of the following active ingredients, of which the list is not intended to limit the invention in any way:

Pyrethroids, such as deltamethrin, cypermethrin, fenpropathrin, cyfluthrin, fenvalerate, permethrin; (thio)phosphoric acid esters, such as triazophos, parathionmethyl, dimethoat, heptenophos, pyrazophos, profenofos, sulprofos, dialifos, chlorpyrifos, anilofos; carbamates, such as BPMC, carbaryl, propoxur, methomyl, carbofuran, phenmedipham, desmedipham, pririmicarb; chlorinated hydrocarbons, such as camphechlor, dicofol; chitin synthesis inhibitors, such as diflubenzuron, trifluron, teflubenzuron (CME 134) or chlorfluazuron (IKI 7899); the agents endosulfan, amitraz, clofentezine, phosethyl AL, prochloraz; herbicides of the phenoxy or heteroaryloxy phenoxy propionic acid derivative type, such as diclofopmethyl, fenoxaprop-ethyl, fluazifopbutyl, haloxyfopethoxyethyl (Dowco 453), quinofopethyl; urea derivatives, such as diuron, isopropturon, linuron, monolinuron, chlortoluron, sulfonyl ureas, such as chlorsulfuron, sulfometuron; triazines such as ametryn, atrazine, simazine; halogenated phenoxy acetic acid or propionic acid derivatives, such as MCPA, dichlorprop, 2,4,5-T, mecoprop, 2,4-D, esters or salts thereof; aniline derivatives, such as butachlor, propanil, benzoylpropethyl, alachlor, metolachlor, nitrophenol derivatives, such as binapacryl or dinosebacetat, nitroaniline derivatives, such as trifluralin or pendimethalin; benzothiadiazines, such as bentazone; the agents ioxynil, bromoxynil, metamitron, glufosinate or salts thereof, bialophos or salts thereof, glyphosate or salts thereof, triazole derivatives, such as triadimefon; the fungicides metal axyl, iprodione, fenarimol, triforine, propiconazol, tridemorph, pyracarbolid; agents containing heavy metals, such as maneb, sineb, triphenyl tin compounds, such as fentin-acetate or fentin hydroxide, azocyclotin, cyhexatin, copperoxy chloride; plant growth regulators, such as mepiquatchloride or chlormequatchloride or similar salts, ancymidol, tetcyclasis or mefluidid. Further information on these treatment agents may be found in CH. R. Worthing, S. B. Walker, The Pesticide Manual, 7th Ed., British Crop Protection Council, London, 1985.

The invention will be illustrated by the following examples, which are not given for purposes of limitation.

EXAMPLES

I. EI Formulation Examples

All quantities are in percent by weight.

Dp. = dropping point
(as determined by DGF method M-III 3)
EO = ethylene oxide        PO = propylene oxide
Br. = boiling range

EXAMPLE 1

30.0% paraffin, Dp. 50–52° C.
2.0% $C_{12}$-$C_{18}$ fatty alcohol + 2 EO
6.0% $C_{16}$-$C_{18}$ fatty alcohol + 6 EO
2.0% $C_{16}$-$C_{18}$ fatty alcohol + 12 EO
60.0% water

EXAMPLE 2

26.0% paraffin, Dp. 50–52° C.
4.0% white spirit, Br. 180–210° C.
2.0% $C_{12}$-$C_{18}$ fatty alcohol + 2 EO
8.0% tallow fatty alcohol + 6 EO
2.0% tallow fatty alcohol + 12 EO
58.0% Water

EXAMPLE 3

23.0% paraffin, Dp. 50–52° C.
2.0% paraffin, Dp. 38–40° C.
10.0% white spirit, Br. 145–200° C.
6.0% tallow fatty alcohol + 6 EO
4.0% $C_{12}$-$C_{18}$ fatty alcohol + 4 EO
1.0% tallow fatty alcohol + 25 EO
54.0% water

EXAMPLE 4

40% paraffin, Dp. 40–42° C.
8% oleyl/cetyl alcohol + 5 EO
52% water

EXAMPLE 5

30.0% paraffin, Dp. 38–40° C.
55.0% xylene
10.5% dodecylbenzene sulfonate, CA salt (70%)
4.5% $C_8$–$C_{10}$/$C_{16}$–$C_{18}$ fatty alcohol mixture + 2 PO + 11 EO

EXAMPLE 6

30.0% paraffin, Dp. 40–42° C.
55.0% xylene
7.5% petroleum sulfonate, Na Salt
7.5% oleic acid + 15 EO

EXAMPLE 7

20.0% paraffin, Dp. 38–40° C.
65.0% white spirit, Br. 145–200° C.
7.5% dodecylbenzene sulfonate, Ca salt (70%)
7.5% oleic acid + 8 EO

EXAMPLE 8

15% microwax, Dp. 68–72° C.
15% paraffin, Dp. 50–52° C.
2% $C_{12}$–$C_{18}$ fatty alcohol + 2 EO
6% $C_{12}$–$C_{18}$ fatty alcohol + 6 EO
2% $C_{12}$–$C_{18}$ fatty alcohol + 12 EO
60% water

EXAMPLE 9

15% paraffin, Dp. 57–60° C.
15% paraffin, Dp. 50–52° C.
2% $C_{12}$–$C_{18}$ fatty alcohol + 2 EO
6% $C_{12}$–$C_{18}$ fatty alcohol + 6 EO
2% $C_{12}$–$C_{18}$ fatty alcohol + 12 EO
60% Water

EXAMPLE 10

30% paraffin, Dp. 50–52° C.
3% $C_{12}$–$C_{14}$ fatty alcohol + 2 EO
5% tallow alcohol + 6 EO
3% tallow alcohol + 12 EO
3% sodium fatty alcohol ether phosphate ($C_{12}$–$C_{18}$ + 10 EO phosphate, 30%)
56% water

EXAMPLE 11

25.0% paraffin, Dp. 57–60° C.
3.0% technical oleyl alcohol + 2 EO
5.0% tallow alcohol + 6 EO
2.0% tallow alcohol + 12 EO
0.1% NaCl
64.9% water

EXAMPLE 12

30% paraffin, Dp. 50–52° C.
3% $C_{12}$–$C_{18}$ fatty alcohol + 2 EO
5% tallow alcohol + 6 EO
3% tallow alcohol + 12 EO
1% sodium fatty alcohol sulfate ($C_8$–$C_{10}$ sulfate, 30%)
2% sodium cumene sulfonate, 50%
56% water

II. Measurement on evaporating water droplets

Water droplets 50 to 100 microns in diameter were sprayed onto 12 micron diameter Perlon fibers and photographed at short intervals under a microscope (500× magnification) in order to record their evaporation behavior at laboratory temperature (22° C.). The diameter and volume of the droplets after various evaporation times were calculated from the micrographs.

Water and a 2.5% aqueous dilution of the evaporation inhibitor of Example 1 were compared with one another.

Under the microscope, a water droplet approx. 70 microns in diameter evaporates completely after 13 seconds at room temperature. After the same time, a droplet of the same diameter containing 2.5% of evaporation inhibitor according to the invention has lost only about one quarter of the its original volume through evaporation.

The times after which the droplets had shrunk to half their original volume or half their original diameter, as determined by linear interpolation between the microscope evaluation dots, are listed in Table 1.

TABLE 1

Measurement of evaporation on droplets

| | Initial diameter | Evaporation time to | |
|---|---|---|---|
| | | half initial volume | half initial diameter |
| Water without inhibitor | 67 microns | 5 seconds | 10 seconds |
| Water containing 2.5% of inhibitor | 64 microns | 18 seconds | 70 seconds |

III. Comparative testing of EI using test mixtures free from active substances (AS)

The following test mixtures were used for testing evaporation inhibition and foaming behavior:

EC - type A:
10 g of AS-free concentrate of 8 g of xylene and 2 g of emulsifier mixture (1.2 g of nonylphenol + 15 EO, 0.8 g of dodecylbenzene sulfonate, Ca salt, 70%) were emulsified in 80 g of water, followed by the addition of 10 g of the inhibitor of Example 1,2,3,4, 8 or 9.
(Blank Value: 10 g of concentrate without inhibitor in 90 g of water).

| EC - type B: |
| --- |
| 10 g of AS-free concentrate of 8 g of phthalic acid diisooctyl ester and 2 g of emulsifier mixture (1.6 g of castor oil + 12 EO, 0.4 g of dodecylbenzene sulfonate, Ca salt, 70%) were emulsified in 80 g of water, followed by the addition of 10 g of the inhibitor of Example 5,6 or 7. |
| (Blank value: 10 g of concentrate without inhibitor in 90 g of water). |

| WP - type: |
| --- |
| 5 g of AS-free wettable powder of 4.4 g of kaolin (bolus alba la, ground) and 0.6 g of emulsifier mixture ($C_{12}$–$C_{14}$ fatty alcohol sulfate, Na salt, inorganic salts) were suspended in 85 g of water, followed by the addition of 10 g of the inhibitor of Example 1,2,3,5, 6 or 7. |
| (Blank value: 5 g of powder without inhibitor in 95 g of water). |

To test the inhibition of evaporation, quantities of 50 g of the spray mixtures were introduced into a plane-bottomed glass dish (diameter 120 mm, height 20 mm) and the evaporation as a function of time produced by a steady stream of air was determined by weighing out at various room temperatures. The results are shown in Tables 2 to 4.

TABLE 2

Tests at 25° C.
Evaporation loss in % by weight

| | ½ h | 1 h | 2 h | 3 h | 4 h | 24 h |
| --- | --- | --- | --- | --- | --- | --- |
| Spray mixture EC - type A | | | | | | |
| Blank value | 9.5 | 15.9 | 27.0 | 37.5 | 48.3 | 97.9 |
| Example 1 | 0.35 | 0.35 | 0.40 | 0.42 | 0.46 | 0.94 |
| Example 2 | 6.8 | 10.8 | 16.1 | 17.3 | 17.7 | 19.1 |
| Example 3 | 0.1 | 0.1 | 0.1 | 0.2 | 0.3 | 1.2 |
| Spray mixture EC - type B | | | | | | |
| Blank value | 9.9 | 15.9 | 29.9 | 42.6 | 64.9 | — |
| Example 5 | 0.1 | 0.1 | 0.1 | 0.1 | 0.2 | — |
| Example 6 | 0.2 | 0.3 | 0.5 | 0.8 | 1.0 | — |
| Example 7 | 0.3 | 0.8 | 1.3 | 1.6 | 1.9 | — |
| Spray mixture WP - type | | | | | | |
| Blank Value | 5.9 | 10.6 | 20.2 | 31.2 | 41.8 | 95.0 |
| Example 1 | 3.8 | 5.5 | 8.6 | 11.7 | 15.3 | 59.5 |
| Example 2 | 1.1 | 2.2 | 4.3 | 6.6 | 9.2 | 44.2 |
| Example 3 | 6.7 | 7.6 | 8.6 | 9.5 | 10.4 | 21.9 |
| Example 5 | 0.2 | 0.3 | 0.4 | 0.5 | 0.6 | — |
| Example 6 | 0.7 | 0.9 | 1.5 | 1.8 | 2.0 | — |
| Example 7 | 0.6 | 0.8 | 0.8 | 0.9 | 0.9 | — |

TABLE 3

Tests at 20° C.
Spray mixture EC - type A
Evaporation loss in % by weight

| | ½ h | 1 h | 2 h | 3 h | 4 h |
| --- | --- | --- | --- | --- | --- |
| Blank value | 10 | 17 | 31 | 45 | 57 |
| Example 1 | 0.4 | 0.4 | 0.4 | 0.4 | 0.5 |
| Example 8 | 0.8 | 1.5 | 2.9 | 5.0 | 6.0 |
| Example 9 | 0.6 | 0.6 | 0.6 | 0.7 | 0.8 |

TABLE 4

Tests at 50° C.
Spray mixture EC - type A
Evaporation loss in % by weight

| | ½ h | 1 h | 1½ h | 2 h | 2½ h | 3 h |
| --- | --- | --- | --- | --- | --- | --- |
| Blank value | 37 | 71 | 92 | — | — | — |
| Example 1 | 20 | 36 | 48 | 53 | 58 | 62 |
| Example 8 | 9 | 16 | 20 | 24 | 27 | 29 |
| Example 9 | 14 | 24 | 31 | 37 | 40 | 42 |

IV. Testing of foaming behavior

To test foaming behavior, the spray mixtures were tested and evaluated by the perforated-disc beating method (DIN 53902).

The results are shown in Table 5.

TABLE 5

Mixture volume 200 ml
Number of beats 30
Temperature 25° C.

Foam volume in ml

| | 30″ | 2′ | 10′ | 30′ | 2 h | 3 h |
| --- | --- | --- | --- | --- | --- | --- |
| Spray mixture EC - type A | | | | | | |
| Blank value | 100 | 80 | 40 | 30 | 10 | — |
| Example 1 | 0 | — | — | — | — | — |
| Example 2 | 5 | 0 | — | — | — | — |
| Example 4 | 0 | — | — | — | — | — |
| Spray mixture WP - type | | | | | | |
| Blank value | 580 | 570 | 550 | 540 | 540 | 540 |
| Example 1 | 70 | 50 | 50 | 40 | 30 | 30 |
| Example 2 | 0 | — | — | — | — | — |
| Example 3 | 10 | 10 | 10 | 10 | 5 | 5 |

V. Comparative testing of EI using commercial products (a) Using the same methods as in Section III, comparative tests were carried out with spray mixtures prepared from commercial concentrates.

The EC used was the insecticide concentrate, Hostaquick ® (a product of Hoechst), which contains 7-chlorobicyclo-(3,2,0)-hepta-2,6-dien-6-yl dimethyl phosphate as its active constituent. The WP used was the fungicide spraying powder, Derosal ® (a product of Hoechst), containing 2-(methoxycarbonylamino)benzimidazole as its active constituent. Table 6 shows the results of the evaporation tests at 25° C.

TABLE 6

Evaporation loss in % by weight

| Spray mixture of | ½ h | 1 h | 2 h | 3 h | 4 h | 24 h |
| --- | --- | --- | --- | --- | --- | --- |
| Hostaquick ® (EC 50) | | | | | | |
| Blank value | 6.3 | 10.3 | 20.3 | 33.7 | 41.7 | — |
| Example 1 | 0.6 | 0.8 | 0.9 | 1.1 | 1.2 | 5.1 |
| Derosal ® (WP 60) | | | | | | |
| Blank value | 8.1 | 19.5 | 29.0 | 45.8 | 67.6 | 95.0 |
| Example 6 | 0.1 | 0.1 | 0.1 | 0.1 | 0.2 | 0.7 |

(b) Further evaporation measurements were carried out as follows using a thermobalance:

To prepare the spraying liquid, the plant protection agents were mixed by shaking with water in the concentrations shown in Table 7, after which the corresponding quantity of inhibitor (Example 1) was added and the mixtures reshaken.

To determine evaporation behavior, quantities of 50 microliters of the spraying liquid were poured into a small cylindrical aluminium dish 6.5 mm in diameter and 1.5 mm deep. The samples were dried in a thermobalance (Du Pont model TGA 951) at 50° C. using a stream of dry air (40 l/h). The weight of the samples was continuously recorded by a recorder.

To calculate the average evaporation rate, the times required to evaporate half the respective sample volumes were taken from the graphs as comparison values.

The volume evaporated divided by the time, based on one square centimeter of evaporation surface, is shown as the average evaporation rate in Table 1. For simplification, the curvature of the evaporation surface was not taken into account in the calculation. The magnitude of the evaporation-inhibiting effect depends to a large extent on the type and concentration of the surfactants in the spray mixture. The fact that the various plant protection agents introduce varying amounts of various surfactants into the spray mixture accounts for the differences in the evaporation-inhibiting effects.

TABLE 7

Average evaporation rate for evaporation to half the original liquid volume.

| Commercial product | product % | inhibitor % | Evaporation rate mg/min per cm² |
|---|---|---|---|
| Water | 100 | 0 | 4.2 |
|  | 90 | 10 | 0.8 |
| Endosulfan 35 EC | 10 | 0 | 4.5 |
| (insecticide) | 20 | 10 | 1.9 |
|  | 10 | 10 | 0.8 |
|  | 5 | 2.5 | 1.5 |
| Triazophos 40 EC | 10 | 0 | 4.4 |
| (insecticide) | 10 | 10 | 0.3 |
|  | 5 | 5 | 0.4 |
|  | 2.5 | 2.5 | 1.3 |
|  | 5 | 2.5 | 0.9 |
| Heptenophos 50 EC | 10 | 0 | 3.6 |
| (insecticide) | 10 | 10 | 0.1 |
| Dichlofopmethyl 36 EC | 10 | 0 | 4.0 |
| (herbicide) | 10 | 2.5 | 0.3 |
|  | 10 | 1 | 0.5 |
| Pyrazophos 30 EC | 10 | 0 | 4.4 |
| (fungicide) | 10 | 10 | 0.8 |

VI. Open-air test

The effect in practice of the reduction in evaporation rate observed in the laboratory was studied in an open-air test under subtropical climatic conditions. The pests Heliothis ssp. and Anthonomus grandis which attack cotton plants were treated at average air temperatures of 38° C. and low humidity levels.

The tests were carried out on two identical 3-hectare parcels planted with cotton which had been pretreated with the usual plant protection agents according to the level of infestation. For the next four applications, the inhibitor of Example 1 was added to the spray mixture applied to parcel 1 while parcel 2 was sprayed without any inhibitor.

The following amounts of plant protection agents per hectare were applied in each of the four sprayings:

| Parcel 1 | Parcel 2 |
|---|---|
| 0.5 l Decis ® (2.5 EC)[1] | 0.5 l Decis ® (2.5 EC) |
| 2.0 l Thiodan ® (35 EC)[2] | 2.0 l Thiodan ® (35 EC) |
| 27.0 l water | 27.5 l water |
| 0.5 l inhibitor |  |

The two parcels were then further treated in exactly the same way. All applications were made by airplane.

At the end of the spraying season, the yields were determined. Parcel 1 yielded 200 kg of cotton per hectare more than Parcel 2, corresponding to an increase in yield of 5% over parcel 2.

(1) EC-concentrate Decis ® contains the insecticide (1R:3S)-3-(2,2-dibromovinyl)-2,2-dimethylcyclopropane carboxylic acid (S)-cyano-3-phenoxybenzyl ester (2) EC-concentrate Thiodan ® contains the insecticide 6,7,8,9,10,10-hexachloro-1,5,5a,9a-tetrahydro-6, 9-methano-2,4,3-benzodioxathiepin oxide as its active constituent.

What is claimed is:

1. An evaporation inhibitor composition consisting essentially of:
   A. from about 15 to about 40% by weight of either
      a. at least one paraffin wax having a dropping point of from about 35° to about 80° C., or
      b. a mixture of waxes containing at least about 50% by weight of at least one paraffin wax having a dropping point of from about 35° to about 80° C.;
   B. from about 4 to about 20% by weight of an emulsifier which is a mixture of at least one nonionic surfactant and at least one anionic surfactant wherein at least 50% by weight of the mixture is nonionic surfactant, the at least one anionic surfactant is at least one of a salt of a sulfuric acid semiester or a phosphoric acid partial ester of a linear alcohol or an alkylphenol containing from 12 to 18 carbon atoms or a polyglycol monoalkylether containing from 12 to 18 carbon atoms in the alkyl group, an olefin sulfonate, ester sulfonate or alkane sulfonate containing from 12 to 20 carbon atoms, an alkylbenzene sulfonate containing from 6 to 16 carbon atoms in the alkyl groups, a sulfonate or polyglycol monoalkylether, and a salt of a polyglycol monoalkylether carboxylic acid containing from 12 to 18 carbon atoms in the alkyl chain, and
   C. from about 35 to about 81% by weight of a solvent or suspending agent which is either
      a. water
      b. an organic solvent having a boiling point of from about 70° to about 280° C. which is one or more of a hydrocarbon, an ester, and a ketone, or
      c. a mixture of a. and b. in any proportion.

2. A composition in accordance with claim 1 wherein the paraffin waxes of component A. have a dropping point of from about 35° to about 70° C.

3. A composition in accordance with claim 1 wherein the paraffin waxes of component A. essentially contain linear $C_{20}$–$C_{40}$ hydrocarbons having an average molecular weight of from about 280 to about 560.

4. A composition in accordance with claim 1 wherein component A. b. contains up to 50% by weight of at least one microcrystalline wax having from 30 to 60 carbon atoms therein.

5. A composition in accordance with claim 4 wherein the at least one microcrystalline wax has an average molecular weight of from about 580 to about 700 and a dropping point of from about 50° to about 90° C.

6. A composition in accordance with claim 1 wherein component B. is present in from about 4 to about 14% by weight.

7. A composition in accordance with claim 1 wherein in component B. the nonionic surfactant is one or more of sorbitan esters of higher fatty acids, long-chain alkyl glycosides, and alkylene oxide adducts with higher, $C_{10}$–$C_{24}$ linear monofunctional or polyfunctional alcohols, alkylphenols, long-chain carboxylic acids, carboxylic acid amides, hydroxy fatty acids, or fatty acid glycerol or sorbitan esters, or long-chain alkyl glycosides.

8. A composition in accordance with claim 7 wherein the nonionic surfactant is one or more of adducts of from 2 to 50 moles of ethylene oxide with a $C_{12}$–$C_{18}$ long-chain primary alcohol or a fatty acid.

9. A composition in accordance with claim 1 wherein the nonionic surfactants in component B are mixtures of ethylene oxide adducts with $C_{12}$–$C_{18}$ fatty alcohols or alkylphenols consisting of

| | |
|---|---|
| from about 10 to about 40% | by weight of adducts containing from 1 to 4 moles of ethylene oxide, |
| from about 25 to about 70% | by weight of adducts containing from 4 to 10 moles of ethylene oxide, |
| from about 5 to about 35% | by weight of adducts containing from 10 to 50 moles of ethylene oxide. |

10. A composition in accordance with claim 1 wherein the component B. the at least one anionic surfactant is one or more of an alkylbenzene sulfonate containing from 6 to 16 carbon atoms in the alkyl group, and an alkane sulfonate containing from 12 to 20 carbon atoms.

11. A composition in accordance with claim 1 wherein up to 5.5% by weight of one or more of a dye, a viscosity regulator, a foam regulator, a preservative, an inorganic salt, a pH regulator, and a hydrotrope is present in the composition.

12. A composition in accordance with claim 1 wherein from about 0.5 to about 10% by weight of the composition is the at least one anionic surfactant of component B.

13. A composition in accordance with claim 1 wherein from composition consists essentially of:
  A. from about 15 to about 40% by weight of either
    a. a paraffin wax having a dropping point of from about 35° to about 70° C. or a mixture of two or more paraffin waxes having different dropping points in the range of from about 35° to about 70° C., or
    b. a mixture of at least one paraffin wax having a dropping point in the range of from about 35° to about 70° C. and at least one microcrystalline wax having a dropping point of from about 50° to about 90° C.;
  B. from about 4 to about 20% by weight of at least one nonionic surfactant, and from 0 to about 10% by weight of at least one anionic surfactant;
  C. from about 35 to about 81% by weight of water, and from 0 to about 10% by weight of one or more of xylene, cyclohexanone, a petroleum fraction having a boiling point in the range of from about 145° to about 210° C., and an ester having a boiling point in the range of from about 70° to about 280° C.;
  D. from 0 to 5% by weight of at least one hydrotrope; and
  E. from 0 to about 0.5% by weight of at least one inorganic salt.

14. An aqueous agricultural spray composition comprising at least one agriculturally active ingredient and from about 1 to about 15% by weight of an evaporation inhibitor composition of claim 1.

15. An aqueous spray composition in accordance with claim 14 wherein from about 5 to about 10% by weight of an evaporation inhibitor composition of claim 1 is present therein.

16. A method for reducing the evaporation of water from an aqueous spray mixture containing at least one agricultural chemical comprising adding thereto from about 1 to about 15% by weight of an evaporation inhibitor composition consisting essentially of:

A. from about 15 to about 40% by weight of either
  a. at least one paraffin wax having a dropping point of from about 35° to about 80° C., or
  b. a mixture of waxes containing at least about 50% by weight of at least one paraffin wax having a dropping point of from about 35° to about 80° C.;

B. from about 4 to about 20% by weight of an emulsifier which is either
  a. at least one nonionic surfactant, or
  b. at least one anionic surfactant, or
  c. a mixture of a. and b. in any proportion; and C. from about 35 to about 81% by weight of a solvent or suspending agent which is either
  a. water
  b. an organic solvent having a boiling point of from about 70° to about 280° C. which is one or more of a hydrocarbon, an ester, and a ketone, or
  c. a mixture of a. and b. in any proportion, and spraying said aqueous mixture onto agricultural crops by the Low-Volume method in a quantity of from about 5 to about 50 liters/hectare.

17. A method in accordance with claim 16 wherein from about 5 to about 10% by weight of said evaporation inhibitor is present therein.

18. A method for treating agricultural crops comprising applying thereto by Low-Volume spraying a treatment-effective quantity of the spray composition of claim 14.

19. A method in accordance with claim 18 wherein the composition of claim 16 is applied to the crops.

20. A method in accordance with claim 18 wherein component A. of the inhibitor composition of claim 1 is selected to have a dropping point from about 10° to about 40° C. above the air temperature prevailing during the application of the inhibitor composition to the crops.

21. An evaporation inhibitor composition consisting essentially of:

A. from about 15 to about 40% by weight of either
  a. at least one paraffin wax having a dropping point of from about 35° to about 80° C., or
  b. a mixture of waxes containing at least about 50% by weight of at least one paraffin wax having a dropping point of from about 35° to about 80° C.;

B. from about 4 to about 20% by weight of an emulsifier which is either
  a. at least one nonionic surfactant, or
  b. at least one anionic surfactant, or
  c. a mixture of a. and b. in any proportion;
  wherein the nonionic surfactant in component B is a mixture of ethylene oxide adducts with $C_{12}$–$C_{18}$ fatty alcohols or alkylphenols consisting of from about 10 to about 40% by weight of adducts containing from 1 to 4 moles of ethylene oxide, from about 25 to about 70% by weight of adducts containing from 4 to 10 moles of ethylene oxide, from about 5 to about 35% by weight of adducts containing from 10 to 50 moles of ethylene oxide, and C. from about 35 to about 81% by weight of a solvent or suspending agent which is either
a. water
b. an organic solvent having a boiling point of from about 70° to about 280° C. which is one or more of a hydrocarbon, an ester, and a ketone, or
c. a mixture of a. and b. in any proportion.

* * * * *

UNITED STATES PATENT AND TRADEMARK OFFICE
CERTIFICATE OF CORRECTION

PATENT NO. : 4,932,994

DATED : June 12, 1990

INVENTOR(S) : Koester, et al.

It is certified that error appears in the above-identified patent and that said Letters Patent is hereby corrected as shown below:

On the front page, left column, at item [73] for Assignee: Read "Henkel Kommanditgesellschaft auf Aktien, Duesseldorf, Fed. Rep. of Germany, and Hoechst Aktiengesellschaft, Frankfurt am Main Fed. Rep. of Germany"

Signed and Sealed this

Fifteenth Day of January, 1991

*Attest:*

HARRY F. MANBECK, JR.

*Attesting Officer*  *Commissioner of Patents and Trademarks*